(12) United States Patent
Park et al.

(10) Patent No.: US 7,215,118 B2
(45) Date of Patent: May 8, 2007

(54) TRANSDUCER FOR GENERATING AND MEASURING TORSIONAL WAVES, AND APPARATUS AND METHOD FOR STRUCTURAL DIAGNOSIS USING THE SAME

(75) Inventors: Chan Il Park, Gyeonggi-do (KR); Seung Hyun Cho, Gyeonggi-do (KR); Soon Woo Han, Seoul (KR); Yoon Young Kim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

(21) Appl. No.: 10/958,590

(22) Filed: Oct. 6, 2004

(65) Prior Publication Data
US 2005/0179430 A1 Aug. 18, 2005

(30) Foreign Application Priority Data
Feb. 16, 2004 (KR) ............ 10-2004-0009887

(51) Int. Cl.
*G01N 27/82* (2006.01)
(52) U.S. Cl. ................... 324/238; 324/240
(58) Field of Classification Search ........ 324/240, 324/207.15, 207.16, 207.17, 238; 73/862.333, 73/862.334, 862.335, 862.336, 622, 643, 73/650, 814, 847, 862.331
See application file for complete search history.

(56) References Cited

U.S. PATENT DOCUMENTS 4,823,620 A * 4/1989 Edo et al. ............ 73/862.334
4,979,125 A * 12/1990 Kwun et al. ............ 702/35
5,581,037 A * 12/1996 Kwun et al. ............ 73/623
6,566,862 B1* 5/2003 Goto et al. ............ 324/207.16
2001/0035749 A1* 11/2001 Nekado ............ 324/207.15

FOREIGN PATENT DOCUMENTS

JP 63-26541 2/1988

OTHER PUBLICATIONS

Kwun et al., Magnetostrictive generation and detection of longitudinal, torsional, and flexural waves in a steel rod, Journal of the Acoustical Society of America, vol. 96, Aug. 1994, pp. 1202-1204.*
Printout from www.m-w.com of the definition of the term "inclination", Merriam-Webster Online, printed Sep. 18, 2006, 2 pages.*
Park et al., "The Generation of Torsional Waves and the Pipe Diagnosis Using Magnetostrictive Transducers." Proceedings of the KSNVE Annual Autumn Conference, pp. 544-548, Nov. 13-14, 2003.

* cited by examiner

*Primary Examiner*—Edward Lefkowitz
*Assistant Examiner*—David M. Schindler
(74) *Attorney, Agent, or Firm*—Dickstein Shapiro LLP

(57) ABSTRACT

A method and an apparatus for structural diagnosis, which generates torsional waves upon a shaft, beam or pipe having arbitrary cross-sections, such as a circular cross-section, and senses existence or location of the cracks through analyzing reflected waves are disclosed. A magnetostrictive transducer comprises a plurality of ferromagnetic strips attached around a circumference of a member having a arbitrary cross-section with a fixed inclination; a first housing disposed to surround the ferromagnetic strips, the first housing being made of insulating material; and a coil would around the first housing. The magnetostrictive transducer can generate torsional waves upon a member when a current is supplied to the coil, and can measure reflected torsional waves.

2 Claims, 5 Drawing Sheets

Fig 1. PRIOR ART
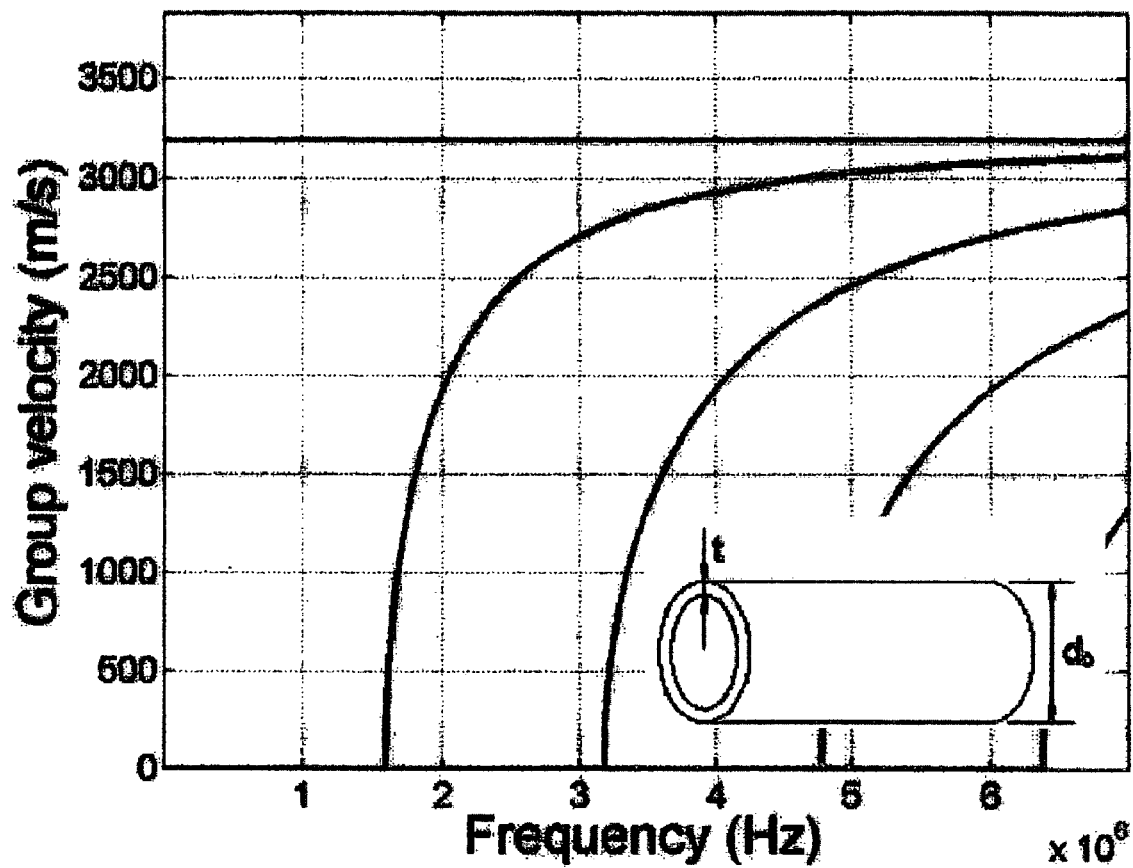
Fig 2 PRIOR ART
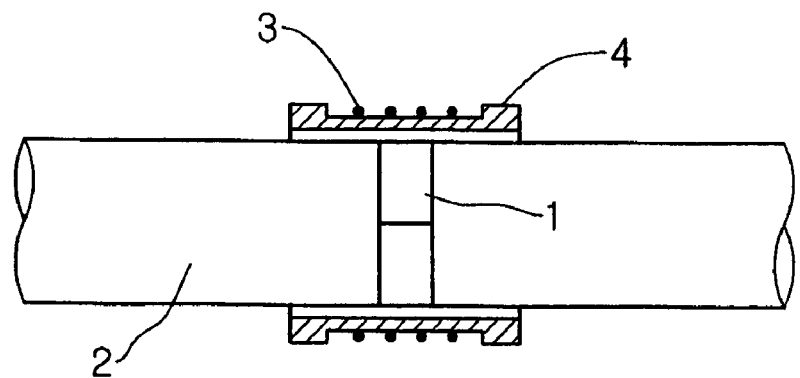

Fig 3a PRIOR ART
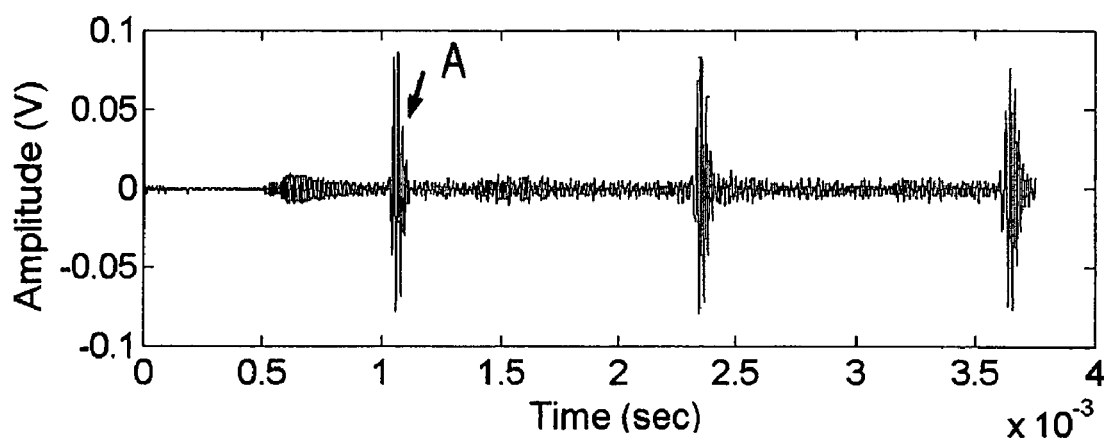
Fig 3b PRIOR ART
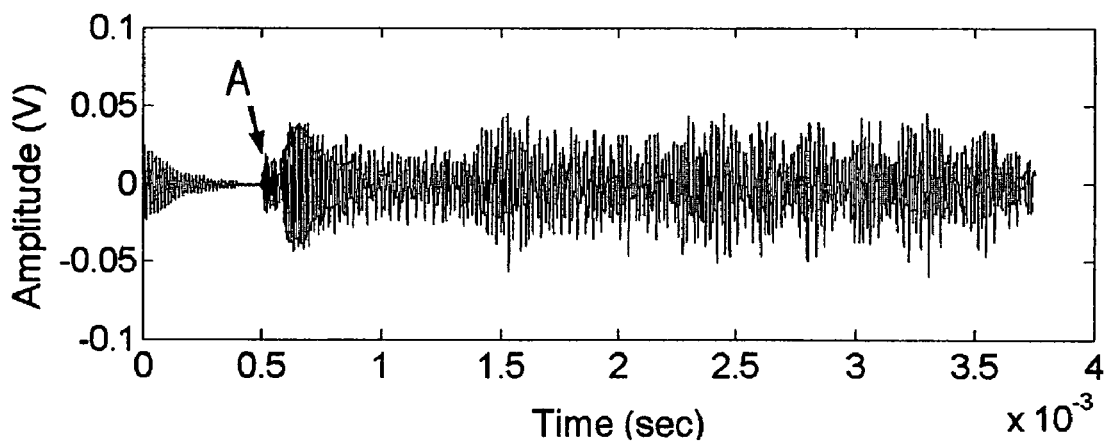

TRANSDUCER FOR GENERATING AND MEASURING TORSIONAL WAVES, AND APPARATUS AND METHOD FOR STRUCTURAL DIAGNOSIS USING THE SAME

CROSS-REFERENCE TO RELATED APPLICATIONS

The entire disclosure of Korean Patent Application No. 10-2004-0009887 filed on Feb. 16, 2004 including specification, claims, drawings and summary is incorporated herein by reference in its entirety.

BACKGROUND OF THE INVENTION

1. Field of the Invention

The present invention relates to an apparatus and a method of nondestructive inspection, which examines whether a shaft, beam or pipe has some cracks. More particularly, the present invention relates to the apparatus and the method for structural diagnosis, which generates torsional waves upon a shaft, beam or pipe having arbitrary cross-sections such as a circular cross-section, and senses existence or location of the cracks through analyzing reflected waves.

2. Background of the Related Art

Magnetostrictive effect, which is also called Joule effect, refers to a phenomenon that mechanical deformation occurs in a ferromagnetic material when the ferromagnetic material is placed in magnetic fields. A reciprocal phenomenon of the magnetostrictive effect (i.e. a phenomenon that changes in magnetic field in vicinity of materials occur when mechanical stress is applied to the materials) is designated as inverse magnetostrictive effect or Villari effect.

The magnetostrictive effect can be expressed as follows:

$$B = \mu_0 H + \mu_0 M = \mu_0 H + \mu_0 \chi_m H = \mu_0 (1 + \chi_m) H = \mu_0 \mu_r H = \mu H \quad \text{[Equation]}$$

where B denotes magnetic flux density, H denotes magnetic field intensity applied by an outside magnet or electromagnet, M denotes magnetization, $\chi_m$ denotes magnetic susceptibility, $\mu_r$ denotes relative permeability, and $\mu$ denotes permeability.

The Joule and Villari effect can be expressed as equations 2 and 3:

$$\varepsilon = \frac{\sigma}{E^H} + q^* H \quad \text{[Equation 2]}$$

$$B = \mu^\sigma H + q\sigma \quad \text{[Equation 3]}$$

where $\varepsilon$ denotes strain, $\sigma$ denotes stress, $E^H$ denotes modulus of elasticity in a constant magnetic field, and $\mu^\sigma$ denotes permeability when constant stress is applied.

The coefficients related to the Joule effect and Villari effect can be represented as equation 4 and equation 5, respectively:

$$q^* = \frac{d\varepsilon}{dH}\bigg)_\sigma \quad \text{[Equation 4]}$$

$$q = \frac{dB}{d\sigma}\bigg)_H \quad \text{[Equation 5]}$$

Magnetostrictive transducers can generate elastic waves of high energy density without physical contact with a test specimen. Therefore, it has been applied to various technical fields. Moreover, it can generate various types of elastic waves such as longitudinal, flexural, and torsional waves only with changes of bias magnetic field.

Among various types of waves, torsional waves are very attractive for the damage detection of the rod or pipe since a first mode of torsional waves has no dispersion. "Dispersion" refers to a phenomenon that waveform of propagating wave is distorted as velocities of waves depend on frequencies.

Nickel is soft magnetic material, that is, it has relatively low hysteresis and small residual flux density. Accordingly, it returns closely to its original status after removing the applied magnetic field. So nickel does not need de-magnetization for repeatability of the transducer, even though, in general, time history affects significantly state of magnetic material.

FIG. 1 is the group velocity dispersion curve of the torsional waves traveling along the aluminum pipe whose thickness($t_s$) is 1 mm, outer diameter($d_0$) is 25 mm, density ($\rho$) is 2800 kg/M$^3$ and modulus of elasticity (E) is 73 GPa.

As can be seen in FIG. 1, a first mode of torsional waves is non-dispersive; therefore, the waveform does not change during its traveling. It is very useful for the long range inspection of a pipe since the traveling time can be measured accurately.

FIG. 2 is a drawing showing structure of the magnetostrictive transducer of the related art, which is used for actuating and measuring the torsional waves.

As illustrated in FIG. 2, the magnetostrictive transducer of the related art is comprised of a thin nickel strip 1 which is bonded around a rod member 2 in a circumferential direction, a non-ferromagnetic housing 4 which is needed to install coil 3.

For detection of cracks in a rod member 2 with the magnetostrictive transducer of the related art, the nickel strip 1 should be pre-magnetized by rubbing a permanent magnet in a circumferential direction (not illustrated). By adjusting the magnitudes of the axially applied magnetic field from the coil, the elastic waves are generated and propagate in the oblique direction, e.g. 45°, with axial direction if the magnitude of the axially applied magnetic field amounts to the magnitude of pre-magnetization in the strip 1. The generated torsional waves travel along the rod member 2 and are reflected from a part where cracks exist, if cracks exist. Then, the reflected torsional waves change the magnetic field around the strip 1.

The variance of the magnetic field induces the electromotive force at the coil by the Faraday-Lenz law, which is described in equation 6. Therefore, the elastic waves propagating along the pipe can be measured by picking out the voltage at the ends of the coil.

$$V(t) = -N\frac{d\Phi}{dt} \quad \text{[Equation 6]}$$

where $\phi$ denotes the total amount of magnetic flux, N denotes the wounded number of the coil, and t denotes the time.

FIG. 3a and FIG. 3b are graphs showing the measured signals of the elastic waves (especially, torsional wave) with the transducer of the related arts. Input currents are 3A in FIG. 3a and 6A in FIG. 3b.

As illustrated in FIG. 3a and FIG. 3b, in the related art it was difficult to send torsional waves with large output power, because the wave pattern measured at the transducer is very sensitive to the input current. When the magnitude of the magnetic field by the input current is increased, the magnitude of the magnetic field by the pre-magnetization with a permanent magnet becomes relatively insufficient for torsional waves. Therefore, besides torsional waves, longitudinal waves are also generated, thus making the measured signal complex as shown in FIG. 3b.

That is, in the related art, if the magnitude of the axially applied magnetic field from the coil and the quantity of pre-magnetization are not well determined, other kinds of waves, besides torsional wave, are also produced. Waveforms of other elastic waves except torsional wave can be considerably changed at the time of being reflected, so that it is not suitable for the other elastic waves to be used in detecting cracks. In addition, as pre-magnetization undergoes time-decay, nickel strip has to be pre-magnetized at every inspection.

Accordingly, for the effective detection of the cracks in the rod, beam or pipe members having arbitrary cross-sections, such as circular cross-section, it is requested that transducer and the diagnosis apparatus using the transducer, which can stably generate large magnitude of torsional wave and secure repeatability, be developed.

The present invention was developed to solve the problems mentioned above. The present invention is to provide an apparatus for structural diagnosis, which can stably generate large magnitude of torsional wave upon a shaft, beam or pipe member having arbitrary cross-sections, such as circular cross-section, without any special pre-magnetization process using a permanent magnet etc., and can detect existence or location of the cracks through analyzing reflected waves.

BRIEF SUMMARY OF THE INVENTION

The present invention relates to apparatus and method of nondestructive inspection, which examines whether a shaft, beam or pipe has cracks. More particularly, the present invention relates to the method and apparatus for structural diagnosis, which generates torsional waves upon a shaft, beam or pipe having arbitrary cross-sections, such as a circular cross-section, and senses existence or location of the cracks through analyzing reflected waves.

According to the present invention, there is provided a magnetostrictive transducer, comprising: a plurality of ferromagnetic strips attached around circumference of a member having an arbitrary cross-section with a fixed inclination; a first housing disposed to surround the ferromagnetic strips, the first housing being made of insulating material; and a coil wound around the first housing, wherein the ferromagnetic strips generate torsional waves upon the member according to magnetostrictive effect when a current is supplied to the coil.

Preferably, the magnetostrictive transducer may further comprise: a second housing disposed to surround the coil at a fixed distance, the second housing being made of insulating material; and a bias coil wound on the second housing, wherein magnitude of the torsional waves is increased by applying a direct current to the bias coil.

Differently, there is provided an apparatus for structural diagnosis comprising: a plurality of ferromagnetic strips attached around circumference of a member having an arbitrary cross-section with a fixed inclination; a first housing disposed to surround the ferromagnetic strips, the first housing being made of insulating material; a coil wound around the first housing; a power source supplying a current to the coil; and a magnetic field measuring device for measuring magnitude of magnetic field in vicinity of the ferromagnetic strips and variation of magnitude of the magnetic field while torsional waves propagate along the member, the magnetic field being induced by applying the current from the power source to the coil, the torsional waves being generated according to magnetostrictive effect.

Preferably, the apparatus for structural diagnosis may further comprise: a second housing disposed to surround the coil at a fixed distance, the second housing being made of insulating material; and a bias coil wound on the second housing, wherein magnitude of the torsional waves is increased by applying a direct current to the bias coil.

Preferably, the magnetic field measuring device may comprise: an amplifier for receiving and amplifying signal of voltage across the coil, the coil being wound around the first housing; an oscilloscope for receiving the signal from the amplifier and displaying variation of the signal according to lapse of time, the signal being amplified by the amplifier; and a computer for receiving data regarding the variation of the signal in shape of digital signal from the oscilloscope and processing the data.

Differently, there is provided a method for structural diagnosis comprising: attaching a plurality of ferromagnetic strips around circumference of a member having an arbitrary cross-section with a fixed inclination and winding a coil around the ferromagnetic strips; generating magnetic field in vicinity of the ferromagnetic strips by applying a current to the coil; making torsional waves propagate along the member, the torsional waves being generated by the ferromagnetic strips according to magnetostrictive effect; recording variance of the magnetic field according to lapse of time while the torsional waves propagate along the member and return from end of the member to a point where the ferromagnetic strips are located after being reflected from the end of the member; and detecting location of crack in the member by figuring out location where magnitude of the magnetic field varies abnormally from the recorded variance of the magnetic field according to lapse of time.

Preferably, the method for structural diagnosis may further comprise increasing magnitude of the torsional wave by adjusting the inclination of the ferromagnetic strips.

BRIEF DESCRIPTION OF THE DRAWINGS

FIG. 1 is a graph showing group velocity dispersion curve of torsional waves traveling along an aluminum pipe.

FIG. 2 is a drawing showing structure of a magnetostrictive transducer of the related art, which is used for actuating and measuring torsional waves.

FIG. 3a and FIG. 3b are graphs showing the measured signals of the torsional waves produced by the transducer of the related arts, respectively.

DETAILED DESCRIPTION OF THE
PREFERRED EMBODIMENTS

Hereinafter, preferred embodiments of the present invention will be described in detail with reference to the accompanying drawings.

Figure 4:
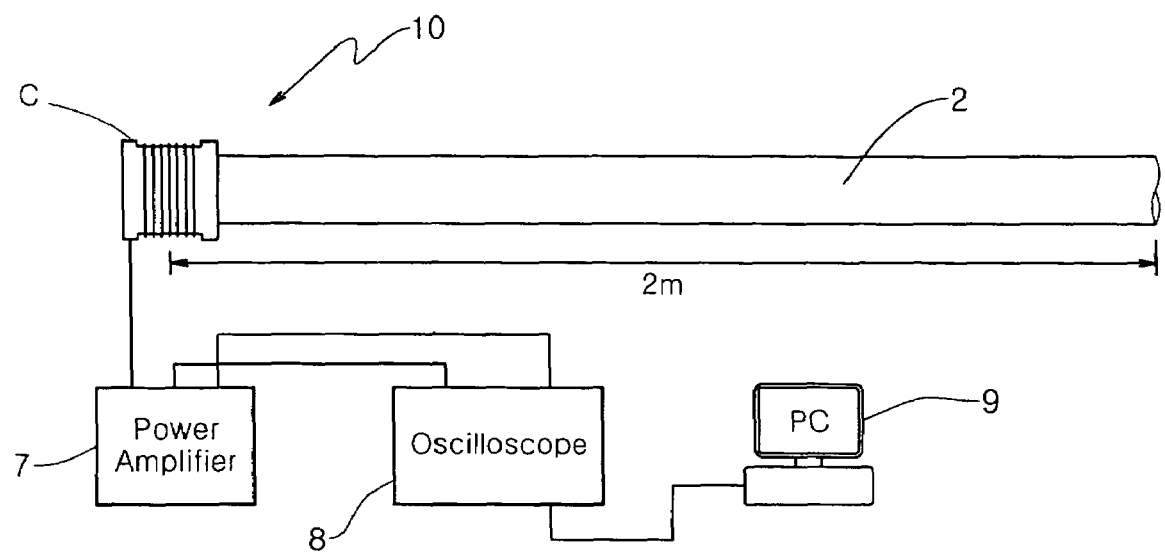
FIG. 4 is a drawing illustrating an apparatus for structural diagnosis according to the present invention.
Figure 5:
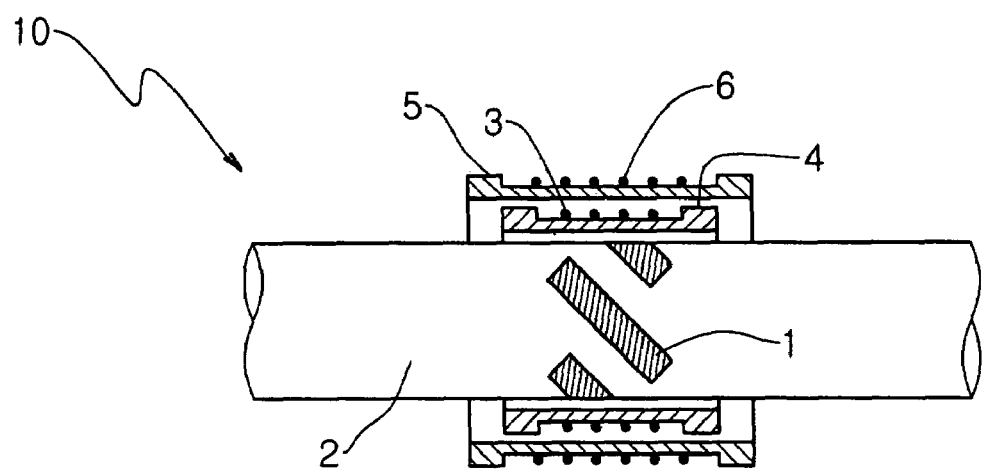
FIG. 5 is a drawing illustrating internal structure of a magnetostrictive transducer according to the present invention.

FIG. 4 is a drawing illustrating an apparatus for structural diagnosis according to the present invention, and FIG. 5 is a drawing illustrating internal structure of a magnetostrictive transducer according to the present invention.

As illustrated in FIG. 4 and FIG. 5, the present invention comprises a plurality of ferromagnetic strips I attached, with a fixed inclination, around circumference of a rod member 2 which has an arbitrary cross-section and fixed length, a coil 3 wound around the ferromagnetic strips 1, a power source supplying a current to the coil, and a magnetic field measuring device for measuring magnitude of magnetic field in vicinity of the ferromagnetic strips and variation of magnitude of the magnetic field while torsional waves propagate along the member, the magnetic field being induced by applying the current from the power source to the coil, the torsional waves being generated according to magnetostrictive effect.

As illustrated in FIG. 4, the magnetic field measuring device comprises: an amplifier 7 for receiving and amplifying signal of voltage across the coil 3, the coil being wound around the first housing; an oscilloscope 8 for receiving the signal from the amplifier 7 and displaying variation of the signal according to lapse of time, the signal being amplified by the amplifier 7; and a computer 9 for receiving data regarding the variation of the signal in shape of digital signal from the oscilloscope 8 and processing the data. The power source is not illustrated in the drawings, because a power amplifier may be used as a power source in this embodiment.

As illustrated in FIG. 5, it is preferred that the present invention further comprises: a second housing 5 to surround a first housing 4 and a coil 3 wound around the first housing 4; and a bias coil 6 wound around the second housing 5. The bias coil 6 is biased by a direct current. Further, the bias coil 6 increases magnitude of the magnetic field, so that magnitude of elastic waves such as torsional waves can be increased, thereby increasing detecting ability of the apparatus for structural diagnosis according to the preferred embodiment of the present invention.

Figure 6A:
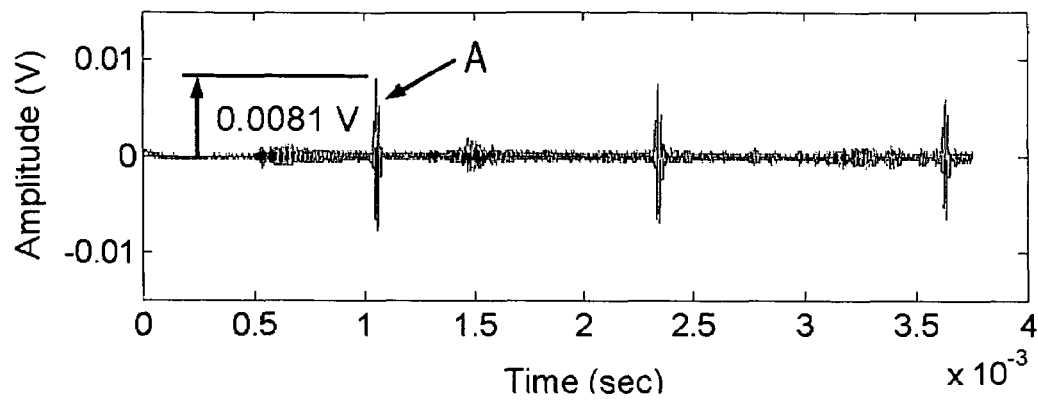
FIG. 6a and FIG. 6b are graphs showing measured signals of torsional waves produced by an apparatus for structural diagnosis according to the present invention.
Figure 6B:
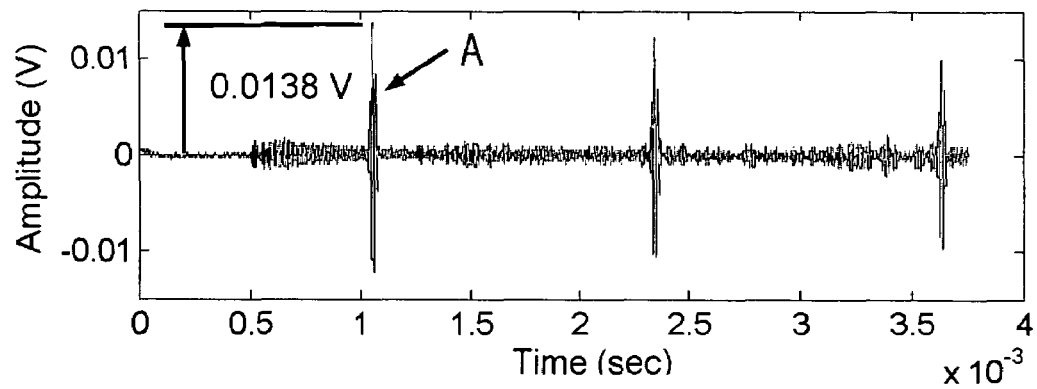

In the apparatus for structural diagnosis according to the present invention, magnetic field is generated in vicinity of the ferromagnetic strips 1 when a current is supplied from the power source to the coil 3. Then, the ferromagnetic strips 1 go through mechanical deformation due to the magnetic field and generate elastic waves upon the rod member 2. Because the ferromagnetic strips 1 are attached to the rod member 2 with a fixed inclination, e.g. 45, torsional waves are generated without pre-magnetization of the rod member 2 using permanent magnet. The torsional waves propagate along the rod member 2 and return from end of the rod member 2 to a part where the ferromagnetic strips are located after being reflected from the end of the rod member 2. If there is a crack in the rod member 2, some of the torsional waves return from a part where the crack exist. When the returned torsional waves come to the part where the ferromagnetic strips are located, the ferromagnetic strips go through mechanical deformation due to the returned torsional waves, thereby resulting in variation of magnetic field in vicinity of the ferromagnetic strips. The variation of magnetic field induces electromotive force ("voltage") across the coil 3. Then, magnitude of the voltage is measured and amplified by the amplifier 7. The amplified voltage is displayed by the oscilloscope 8 and transferred to the personal computer 9. The personal computer 9 receives data regarding the amplified voltage in shape of digital signal and processes the data. FIG. 6a and FIG. 6b illustrate the measured voltages according to lapse of time.

FIG. 6a and FIG. 6b show experimental results, which are measured at aluminum cylindrical pipe whose outer diameter is 25 mm, thickness is 1 mm and length is 2000 mm. A transducer used in these experiments is fabricated by disposing at one end of the cylindrical pipe a hollow cylinder type case whose outer diameter is 28 mm and inner diameter is 26 mm, and winding enamel coil, whose diameter is 0.3 mm, 64 times around the hollow cylinder type case to make width of winding part of the hollow cylinder type case be 19.2 mm. A nickel strip used in the experiments is manufactured to have size of 25 mm in length, 3 mm in width and 0.15 mm in thickness. The nickel strip is attached to the cylindrical pipe with an adhesive agent like epoxy, having inclination with axis of the cylindrical pipe. While the inclination is about 45° in the drawings, the inclination according to the present invention is not limited to 45°. Inclination that can produce torsional wave through the deformation of the ferromagnetic strips without any pre-magnetization process will suffice.

The input current to the coil is 4.75 A in FIG. 6a whereas the currents of 8.44 A is supplied to the coil in FIG. 6b. From these two graphs, it is clear that the torsional waves reflected at end of the pipe can be measured well and output of the transducer increases, as magnitudes of the input currents increases. The input signal in this example has form of a single sinusoidal wave with center frequency of 40 kHz, however, any shapes of wave can be used according to purpose of tests.

Hereinafter, an apparatus for structural diagnosis using a transducer for generating and sensing torsional waves according to a preferred embodiment of the present invention will be described.

Figure 7:
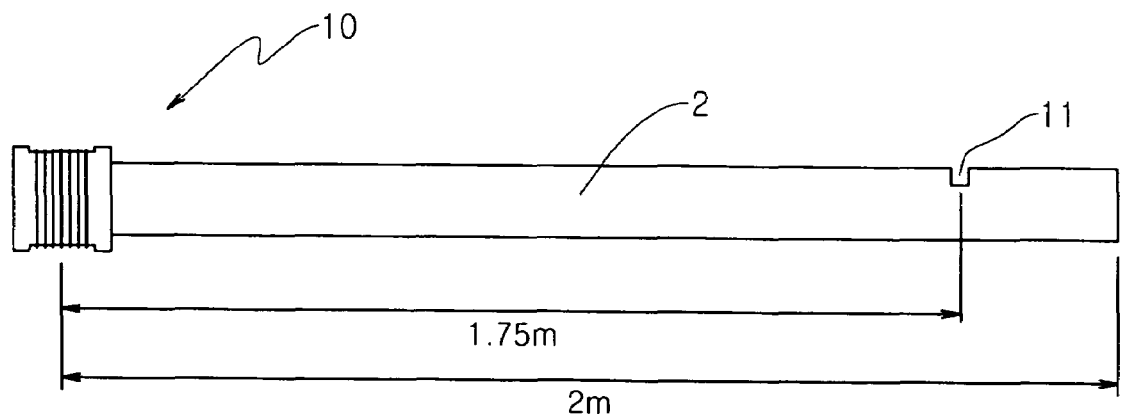
FIG. 7 is a drawing illustrating an apparatus for structural diagnosis according to the present invention, which is installed on a pipe with a crack.
Figure 8:
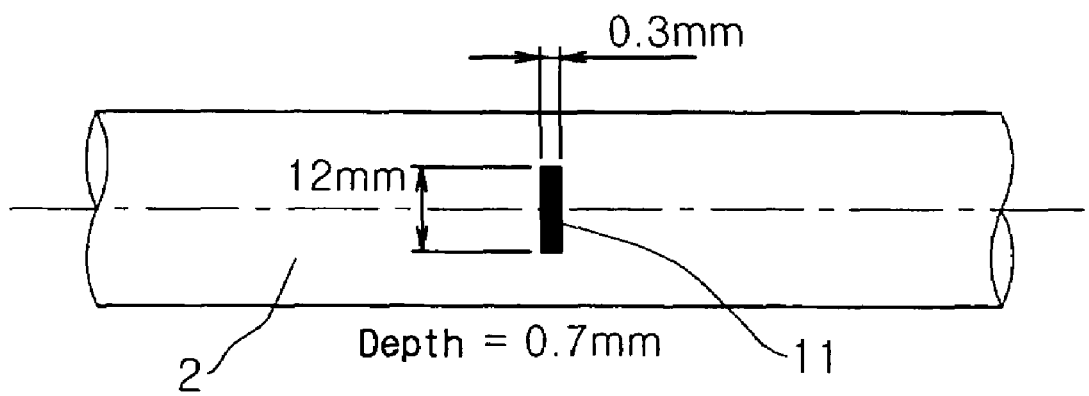
FIG. 8 is a drawing illustrating dimension of a crack at a pipe.

FIG. 7 illustrates that the apparatus for structural diagnosis according to the present invention is installed at one end of a pipe having a crack. FIG. 8 illustrates dimension of the crack made artificially in the pipe illustrated in FIG. 7.

The pipe used in this preferred embodiment is an aluminum pipe whose outer diameter is 25 mm, thickness is 1 mm and length is 2000 mm. The transducer is installed at the end of the pipe and distance between the transducer and the crack is 1750 mm.

Torsional waves generated by the transducer travel along the pipe and some parts of them will be reflected at the crack and return to the transducer. Therefore, location of the crack 11 can be estimated by analyzing signal measured at the transducer considering velocity of the torsional waves in the pipe.

The distance between the transducer and the crack can be estimated as follows:

$$d^{estimated\ crack} = c \times \Delta t / 2 \qquad \text{[Equation 7]}$$

where c denotes velocity of the torsional wave, and $\Delta t$ denotes traveling time of the torsional waves from the crack to the transducer.

Figure 9:
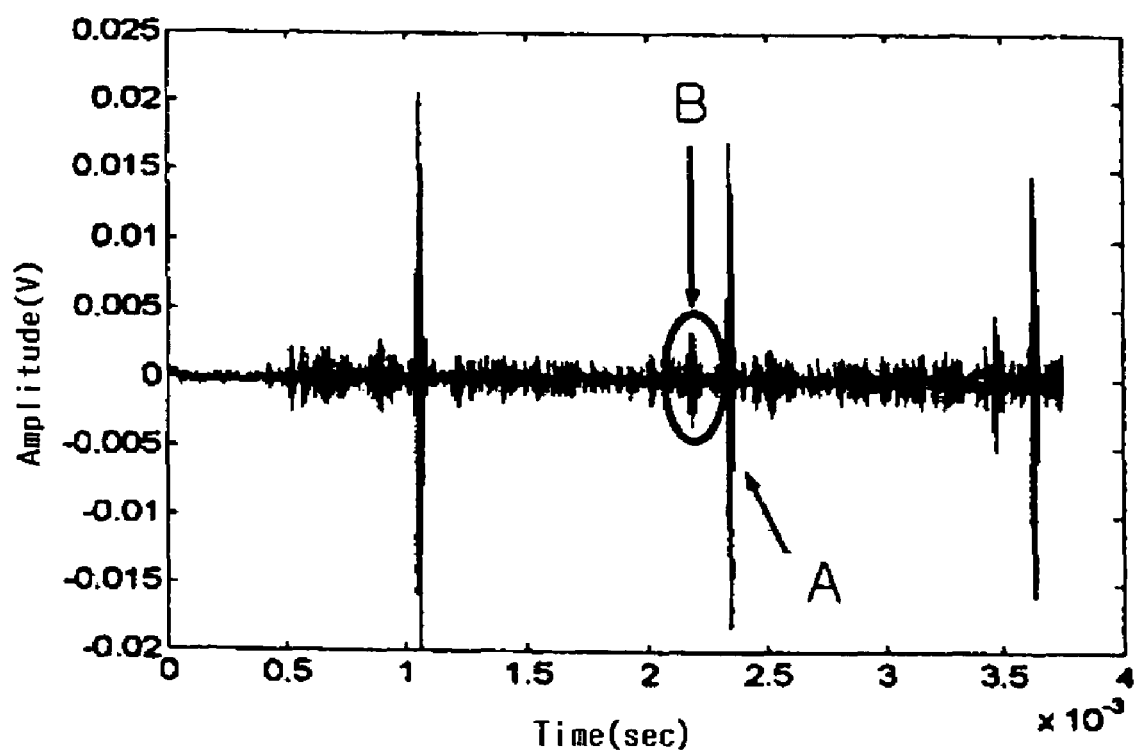
FIG. 9 is a graph showing the measured signals of the torsional waves according to the present invention comprising the transducer shown in FIG. 7.

FIG. 9 illustrates the torsional waves measured at the pipe using the transducer shown in FIG. 7.

As can be seen in FIG. 1, group velocity of a first mode of torsional waves in the pipe is 3094 m/s. From the velocity and traveling time of the torsional waves reflected from the crack, the distance between the crack and the transducer can be estimated as 1730 mm. Considering the actual distance of 1750 mm, estimation accuracy is quite good and the error is only 1.5%, which reveals excellent performance of the apparatus based on the present invention.

As illustrated above, the present invention provides a magnetostrictive transducer, which can stably generate and measure torsional waves in a member made of non-ferromagnetic material such as aluminum.

In the magnetostrictive transducer for generating and measuring torsional waves according to the present invention, nickel strips are attached to a member with a fixed inclination, e.g. 45° with axis of the member, which may generate torsional waves without pre-magnetization of the nickel strips. Moreover, the transducer can stably generate torsional waves, irrespective of magnitudes of input currents, which cannot be achieved in the related art.

The forgoing embodiment is merely exemplary and is not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. An apparatus for structural diagnosis comprising;
    a plurality of ferromagnetic strips attached around a circumference of a member having an arbitrary cross-section with a fixed inclination;
    a first housing disposed to surround the ferromagnetic strips, the first housing being made of insulating material;
    a coil wound around the first housing;
    a second housing disposed to surround the coil at a fixed distance, the second housing being made of insulating material; and
    a bias coil wound on the second housing,
    a power source supplying a current to the coil wound around the first housing and the bias coil; and
    a magnetic field measuring device for measuring the magnitude of a magnetic field in the vicinity of the ferromagnetic strips and a variation of the magnitude of the magnetic field while torsional waves propagate along the member, the magnetic field being induced by applying the current from the power source to the coil wound around the first housing, the torsional waves being generated according to a magnetostrictive effect;
    wherein the bias coil is adapted to increase the magnitude of the torsional waves responsive to an application of a direct current to the bias coil.

2. The apparatus for structural diagnosis of claim 1, wherein the magnetic field measuring device comprises;
    an amplifier for receiving and amplifying a signal of voltage across the coil wound around the first housing, the coil being would around the first housing;
    an oscilloscope for receiving the signal from the amplifier and displaying variation of the signal according to lapse of time, the signal being amplified by the amplifier; and
    a computer for receiving data regarding the variation of the signal from the oscilloscope and processing the data.

* * * * *